United States Patent [19]

Bradley et al.

[11] Patent Number: 4,543,141
[45] Date of Patent: Sep. 24, 1985

[54] METHOD OF MAKING ELASTIC DIAPERS, APPARATUS THEREFOR, AND PRODUCT

[75] Inventors: John J. Bradley, Green Bay; Debra K. Hansen, Maribel, both of Wis.

[73] Assignee: Paper Converting Machine Company, Green Bay, Wis.

[21] Appl. No.: 565,227

[22] Filed: Dec. 27, 1983

[51] Int. Cl.⁴ .............................................. A61F 13/16
[52] U.S. Cl. .................................... 156/164; 156/201; 156/229
[58] Field of Search ............... 156/164, 229, 495, 461, 156/200, 201, 202, 204, 269; 112/121.26, 121.27

[56] References Cited

U.S. PATENT DOCUMENTS

| 4,081,301 | 3/1978 | Buell | 156/164 |
| 4,300,967 | 11/1981 | Sigl | 156/164 |
| 4,353,762 | 10/1982 | Bouda | 156/164 |

*Primary Examiner*—William R. Dixon, Jr.
*Assistant Examiner*—Ann M. Knab

[57] ABSTRACT

A method for producing elastic disposable diapers, apparatus therefor and product therefrom which includes applying a continuous stripe of adhesive to stretched elastic ribbon, V-folding longitudinally spaced portions of the ribbon to immobilize the adhesive in the spaced portion, applying the intermediate flat portions of the stretched ribbon with exposed adhesive to a substrate, to form discrete diapers which have contractable portions therein.

12 Claims, 10 Drawing Figures

METHOD OF MAKING ELASTIC DIAPERS, APPARATUS THEREFOR, AND PRODUCT

This invention relates to a method of making elastic diapers, apparatus therefor and product, and, more particularly, to a diaper of the disposable variety wherein discreet portions of the elastic ribbon are V-folded to limit the amount of puckering of the diaper.

BACKGROUND OF THE INVENTION

The basic teaching for the manufacture of an elastic leg band diaper is found in U.S. Pat. No. 4,081,301 and consists of stretching the elastic ribbons, maintaining tension therein, and intermittently applying adhesive to selected portions of the elastic corresponding to the contractable leg portion of the diaper. Intermittent operation of devices used for applying adhesives is commonly accepted—but requires adhesives within a fairly narrow range of viscosity since the adhesive must be responsive to on-off operation of the nozzles or other applying means. Because the adhesive in such a situation must be fluid enough to be responsive, it lacks the higher tack characteristic of more desirable adhesives having higher viscosity. These more desirable adhesives, if used in on-off situations, cause plug-up and stringing problems, require sensitive heat control and expensive applying devices.

However, limiting the length of ribbon adhered to the underlying web results in that only selected portions of the diaper are shirred or gathered when the ribbon tension is relaxed. Further, the non-glued portions of the ribbon due to being unattached, do not cause gathering and also, upon relaxation of tension, retreat to normal length and are hidden inside the diaper.

On the other hand, with adhesives having higher viscosities and therefore higher tack, which could be used if the adhesive stripe were put down continuously, the deleterious effects of creep or slippage on the long term storage exposure to higher temperatures are avoided. However, the prior art expedients relative to continuous glue application involve either much higher cost materials or the addition of a release medium which must also be placed on the substrate intermittently.

For example, U.S. Pat. No. 4,300,967 teaches the use of a thermoplastic elastomeric material for the continuous ribbon and requires special equipment including heated rolls, chill rolls, etc., to immobilize or render inert spaced portions of the adhesive equipped elastic ribbon which correspond to the ends of the diaper.

U.S. Pat. No. 4,353,762 teaches the use of a release medium applied to intermittent spaced portions of the moisture impervious web while the adhesive is applied continuously to the stretched ribbon. Thereafter, the ribbon adheres almost instantaneously to the impervious web but will not adhere to those portions covered with the release medium. However, this again requires complicated equipment and the expenditure of additional money for materials not needed. In both cases, there is a "canceling out" of the activity of the adhesive.

SUMMARY OF THE INVENTION

The invention departs from the previous expedients in not performing some additional expensive and complicated operation to "cancel out" the activity of the adhesive, but rather uses the adhesive itself to achieve non-adherence in longitudinally spaced portions of the underlying moisture impervious web. More particularly, after the continuous stripe of adhesive is laid down on the flat ribbon, intermittent portions are "V-folded", i.e., longitudinally folded on itself to provide longitudinally spaced portions of the ribbon which are incapable of adherence to the underlying web. Although the invention utilizes synchronized processing for intermittent attachment of the pre-stretched elastic ribbon, the method of control and devices are greatly simplified over the prior art. Further, because adhesive can be applied in a continuous stripe, a wider range of adhesives having more desirable tack characteristics can be used without concern over possible incompatibility with the media to which they are attached.

The invention is described in conjunction with the accompanying drawing, in which.

DETAILED DESCRIPTION

Figure 1:
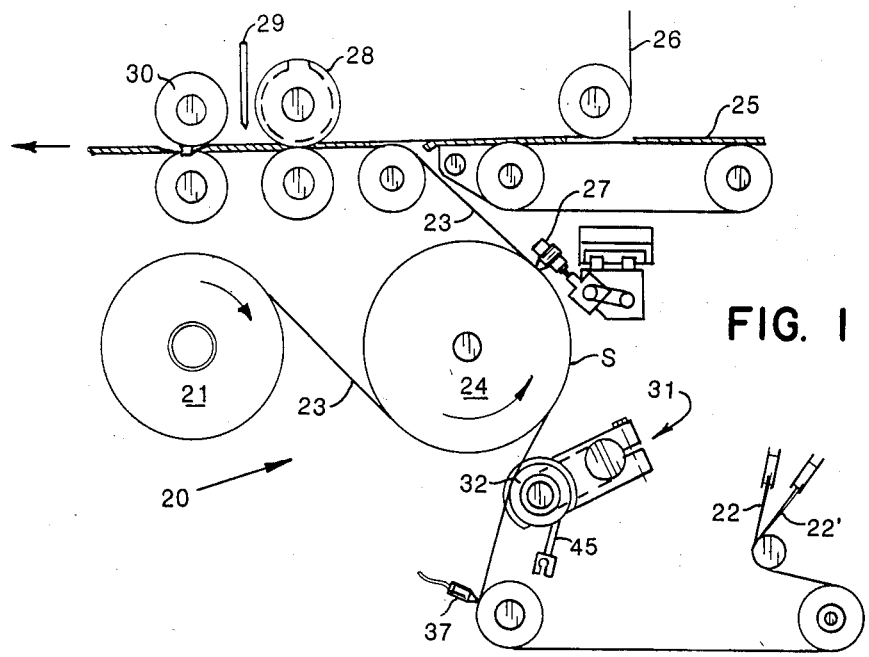
FIG. 1 is a side elevational view of apparatus depicted schematically for the production of elasticized leg band disposable diapers.

In the illustration given and with reference first to FIG. 1, the numeral 20 designates generally apparatus for the production of elastic leg band diapers. Such apparatus generally is well known and normally includes side frames (not shown) for the purpose of supporting the various rolls in conventional fashion.

OPERATION GENERALLY

For example, the outermost layer of the diaper is normally constructed of 0.5 mil thickness polyethylene to provide the moisture impervious barrier for the diaper. A parent roll of such material is designated in FIG. 1 by the numeral 21 (see the central left hand portion) which is advanced toward a ribbon uniting station S—where it will be equipped with a pair of ribbons 22 and 22' (see the right hand portion of FIG. 1). These are advanced toward the station S and there joined to the poly web 23—on the surface of a bedroll 24. In some instances the roll 24 may have a heat dissipating characteristic which advantageously can be provided in the form of a chill roll.

Figure 7:
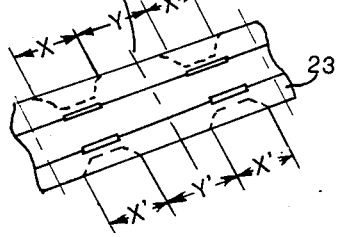
FIG. 7 is a fragmentary perspective view of a portion of a diaper after the elastic ribbons have been applied thereto.

At this stage, the continuous web has the appearance of that seen in FIG. 7. The dotted line portions represented by the symbol "X" are those ultimately cut out of the continuous web to form the crotch portions of the diaper. It will be noted, however, that the elastic ribbons 22 and 22' extend longitudinally of the polyethylene web 23.

Proceeding upwardly and to the left in FIG. 1 from the bed roll 24, the now integrated polyethylene web 23 and elastic ribbons 22, 22' meet with a series of absorbent batts 25 which are confined against the polyethylene web by a nonwoven (moisture pervious) web 26. The webs 23 and 26 are united by virtue of adhesive previously laid down on the web 23 by a glue applying nozzle 27—see the central portion of FIG. 1. Rolls 28 equipped with marginal pressure rings effect the union of the webs 23 and 26.

Thereafter, the cutouts "X" are made by a water jet nozzle 29—see the upper left hand portion of FIG. 1—and ultimately the now completed diaper web is transversely severed by means of cutoff rolls 30.

Within the purview of the invention is the alternative procedure illustrated in U.S. Pat. No. 4,081,301 wherein the absorbent batts are laid down on the poly web before the elastic ribbons are united to the poly web in the crotch portions of the diaper.

RIBBON FOLDING

The intermittent longitudinal folding of the ribbons 22, 22' is accomplished by the mechanism generally designated 31 in the lower central portion of FIG 1. One of the folding rolls 32—for one of the ribbons 22, 22' is seen in perspective view in FIG. 2. There, the roll 32 is seen to have a first cylindrical surface 33 and a second cylindrical surface 34—which has a greater radius. Additionally, the arcuate segment 35 providing the surface 34 is equipped with a circumferentially extending groove or slot 36 which performs the function of V-folding the ribbon longitudinally on itself. At the time the ribbons 22, 22' encounter the folding rolls 32, they have already been equipped with a stripe of adhesive provided by the nozzle 37—see the lower central portion of FIG. 1.

Figure 3:
FIGS. 3-6 are a series of schematic side elevational views showing the steps of intermittently folding the ribbon after adhesive has been applied thereto.

FIGS. 3–6 illustrate schematically the operation of the folding rolls 32. In FIG. 3, the ribbon 22 is seen to be in contact with the reduced diameter surface 33— hence, no folding occurs. The folding roll 32 is rotating in the same direction as the web ribbon 22 but optionally at a greater speed. We have found it advantageous to have a speed differential between the rolls 32 and the ribbon 22, 22'. This may be achieved in a variety of ways but the preferred form is to have the roll travel at about 25–50% faster than the ribbon.

Figure 2:
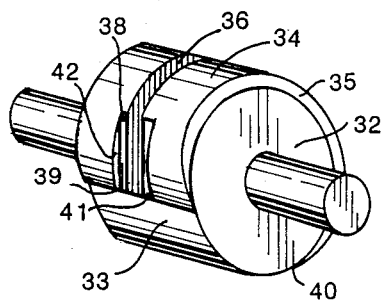
FIG. 2 is a fragmentary perspective view of the folding roll employed in the practice of the invention and which is seen in the central lower right hand portion of FIG. 1.
Figure 4:
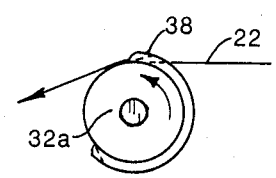
Figure 5:
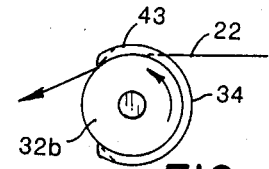
Figure 6:
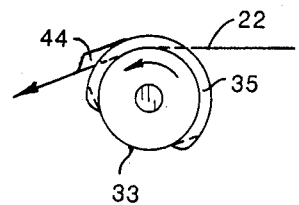

In FIG. 4, the folding roll is now in the condition designated 32a and it is seen that the ribbon 22 has now entered the pilot entrance or transition 38—see particularly FIG. 2. While the leading edge 39 and the trailing edge 40—still referring to FIG. 2—of the raised segment 35 can be gradually sloped to extend from the surface 33 to the surface 34, it has been found useful to provide the pilot entrance 38 to the slot 36. The entrance 38 includes sloped surfaces as at 41 and flanking sidewalls 42. Similar machining and treatment is added to the trailing portion 40. The pilot entrance 38 including the inclined surfaces 41 and the side vertical flanking surfaces 42 is sized such that the distance between the vertical side surfaces is substantially equal to the non-folded stretched ribbon width. The flat ribbon enters the pilot entrance 38, rides up on the inclined surfaces 41 and straddles groove 36 as the leading portion of the upraised segment 35 contacts the stretched ribbon. Almost instantaneously thereafter, the stretched ribbon is forced into a V-folded configuration by entering the slot 36. When the upraised segment 35 passes beyond contact with the ribbon, the ribbon is no longer contained by the slot 36 and the ribbon is now flat and contacts the reduced diameter cylindrical surface 33.

More particularly, in FIG. 4, the stretched ribbon is shown at the instant of contact with the inclined surface 41. On further rotation of the rolls 32 to the condition 32B in FIG. 5 the inclined portions 41 urge the flat ribbon upwardly from the surface 33 and radially outward to a point 43. At this instant, the flat ribbon straddles the slot 36 but because of its stretched condition, and lacking support in the center thereof, the stretched ribbon tends to assume the previous straight line condition and in so doing, enters the slot 36 and into the V-folded relationship shown at 44 in FIG. 6. Once in the groove, the stretched ribbon maintains the V-folded configuration until the enlarged segment 35 ends. At that point, the unsupported sides of the stretched ribbon will again lay flat on the surface 33 and remain thereon until encountering once again the enlarged segment 35.

It will be recognized that the above description is intended to explain the general operation of the ribbon folding operation. If the pilot entrance 38 to the slot 36 is shaped differently, for example, sloped inwardly toward the apex of the folding groove at the same time it is sloped upwardly, it is possible that the stretched elastic falls into the grooves before reaching the outer periphery 43 and it would not straddle the groove before being contained therein. In essence, and depending on the shape and configuration of the pilot entrance, the folding operation is accomplished while the stretched elastic ribbon is guided toward the slot, and the actual instant of fold over is not of significant effect or consequence. The trailing edge of the slot can be altered to include inclined surfaces similar to those at 41 in order to allow a gradual transition to a flat non-folded ribbon configuration.

Figure 8:
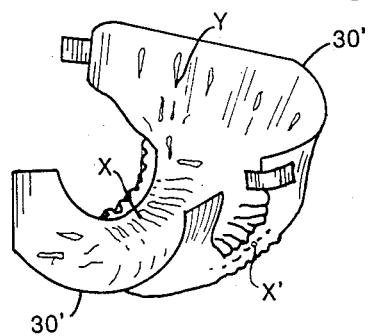
FIG. 8 is a perspective view of a diaper made according to the teachings of this invention.

This results in the lay flat portion of the ribbons 22 and 22' being confined to the area designated X, X' in FIG. 7. The folded portions occupy the distance designated Y, Y'. So, when a cut occurs midway of the length of dimension Y, Y'—as at 30' in FIG. 7—a discreet diaper is provided of the nature seen in FIG. 8. There, only the central or crotch portions are puckered or shirred and the unsecured, i.e., V-folded portions of the ribbon lie in the unpuckered waist portion of the diaper. As mentioned above, these retract to their normal, unextended length, so that there are no ends discernible along the lines 30'.

In the practice of the invention, the elastic ribbon which normally has an untensioned width of about $\frac{1}{4}"$ and a thickness of 0.10", reduces to about 3/16" in width. This, however, provides sufficient width for the 1/16" wide stripe or bead or adhesive put down by the nozzle 37. In some instances the ribbon width may be more or less and, in such case, the other dimensions given above will change correspondingly.

For example, the instant invention can be used to advantage in the co-owned diaper waist band method and apparatus application of Harvey J. Spencer, Ser. No. 569,172 filed Jan. 9, 1984. In such a case, the stretched ribbon or ribbons are wider and severed prior to union with the moisture impervious web.

In the illustration given in FIG. 1, a scraper blade 45 is shown in contact with the reduced diameter surface of the roll 32—and as the roll rotates, the blade is effective in scraping slot 36 which is machined to a depth equal to the radius of surface 33. Other types of heated scrapers or doctors, felt wipers, or a rotary blade having a thickness equal to the width of the slot 36 can be employed and all will effectively keep the slot free of contaminants on a continuous basis while the machine is operating. The width of the slot 36 is advantageously slightly greater than two times the thickness of the stretched elastic ribbon 22 and the depth from the surface 34 to the surface 33 is advantageously about one half the width of the flat stretched ribbon.

Figure 9:
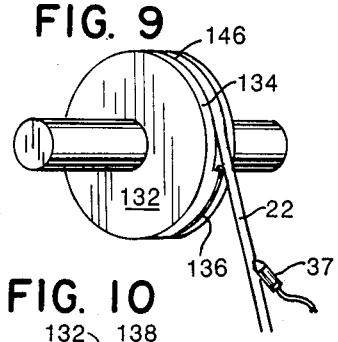
FIG. 9 is a fragmentary perspective view of apparatus employed in the practice of the invention and which features the preferred form of folding roll.
Figure 10:
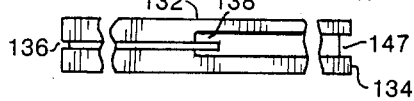
FIG. 10 is a fragmentary top plan view of the folding roll of FIG. 9.

Reference is now made to FIGS. 9 and 10 which illustrate the preferred form of folding roll employed in the practice of the invention. The roll 132 has an outer cylindrical surface 134. Provided in the surface 134 is a slot 146. The slot 146 includes two different portions 136 and 147. The slot portion 136 corresponds in width to the slot 36 of the FIG. 2 showing. The slot portion 147 is wider to accommodate the unfolded width of the stretched elastic ribbon 22 or 22' as the case may be. The showing of FIGS. 9 and 10 is preferred because of ease of manufacture. Other V-folds forming devices may also be employed.

In the showing of FIGS. 9 and 10 the bottom of the slot portion 147 corresponds to the surface 33 of roll 32 in FIG. 2. In the roll 132, there is provided a transition or pilot entrance 138—see particularly FIG. 10.

In the practice of the invention employing the folding roll 132 of FIGS. 9 and 10, a speed was realized corresponding to 600 diapers/minute with satisfactory performance. The speed differential was 35%, greater i.e., the speed of the outer surface 134 was 35% than the speed of the stretched elastic ribbon 22. The circumferential length of the slot portion 136 was 180° with the slot portion 147 occupying the remaining 180°. In addition, the roll 132 was driven at a rate of one revolution per diaper.

In some instances, it may be advantageous to put a hard, slippery surface on those areas contacting the elastic ribbons. The ribbons usually are provided with a talc coating which can be quite abrasive. Also the roll 132 should be as close as possible to the uniting roll 24 to reduce the possiblity of ribbon twist.

We claim:

1. A method of securing longitudinally spaced portions of a stretched, flat faced elastic ribbon to a continuously moving web, the steps of:
    applying a continuous stripe of adhesive to one face of said ribbon,
    V-folding longitudinally spaced portions of said ribbon to bring the parts of said one face into confronting relation and to provide a series of longitudinally spaced non-folded portions, and
    securing said non-folded portions to said web.

2. The method of claim 1 in which said ribbon is transversely severed between adjacent non-folded portions.

3. The method of claim 2 in which said ribbon and web are simultaneously transversely severed.

4. The method of claim 2 in which said ribbon is transversely severed prior to securing said ribbon to said web.

5. The method of claim 2 wherein said severing occurs substantially midway of the length of each folded portion.

6. The method of claim 1 in which said V-folding step includes moving said ribbon through the slot of a slot-equipped member, said slot having a width slightly greater than twice the thickness of said stretched ribbon and a depth sufficient to develop V-folding of said stretched ribbon and where there is relative movement between said slot and said stretched ribbon.

7. The method of claim 6 in which said slot is moved at a speed approximately 25–50% greater than said stretched ribbon.

8. A method of securing longitudinally spaced portions of a stretched, flat faced elastic ribbon to a continuously moving web, the steps of:
    applying a continuous strip of adhesive to one face of said ribbon,
    V-folding longitudinally spaced portions of said ribbon to bring the parts of said one face into confronting relation and to provide a series of longitudinally spaced non-folded portions,
    securing said non-folded portions to said web, and
    transversely severing said web and ribbon between adjacent non-folded portions whereby said non-folded portions selectively contract the web.

9. A method of manufacturing an elastic leg band disposable diaper comprising:
    advancing a moisture impervious web toward a ribbon uniting station,
    advancing a pair of stretched, flat faced elastic ribbons toward said station and prior to reaching said station,
    applying a continuous stripe of adhesive to one face of each of said ribbons,
    V-folding longitudinally spaced portions of each of said ribbons in synchronization to bring the parts of said one face into confronting relation and to provide a series of longitudinally spaced non-folded portions of said ribbon,
    securing in synchronism at said station said non-folded portions to said web,
    intermittently supplying absorbent batts to said web and thereafter applying a moisture pervious web to said batts and web and securing both of said webs together along longitudinal, marginal lines, and
    transversely severing said webs and ribbons between adjacent non-folded portions of said ribbons whereby said non-folded portions selectively contract the crotch-providing area of a diaper developed from said webs.

10. The method of claim 9 in which said ribbon is about ¼" in width.

11. The method of claim 9 in which said adhesive is of a high viscosity, high tack characteristic.

12. A method of manufacturing an elastic leg band disposable diaper comprising:
    advancing a moisture impervious web toward a uniting station and intermittently securing absorbent batts to said web,
    advancing a pair of stretched, flat faced elastic ribbons toward a ribbon uniting station and prior to the reaching said ribbon uniting station,
    applying a continuous stripe of adhesive to one face of each of said ribbons,
    V-folding longitudinally spaced portions of each of said ribbons in synchronization to bring the parts of said one face into confronting relation and to provide a series of longitudinally spaced non-folded portions in said ribbon, securing in synchronism at said station and said non-folded portions to said web,
    applying a moisture pervious web to said batts and web and securing both of said webs together along longitudinal, marginal lines, and
    transversely severing said webs and ribbons between adjacent non-folded portions of said ribbons whereby said non-folded portions selectively contract the crotch-providing area of a diaper developed from said webs.

* * * * *